United States Patent [19]
Hoffmann et al.

[11] 3,976,666
[45] Aug. 24, 1976

[54] REMOVAL OF DEACTIVATING DUST PARTICLES FROM FIXED BED CATALYSTS IN THE VAPOR PHASE OXIDATION OF NAPHTHALENE TO PHTHALIC ANHYDRIDE

[75] Inventors: Gunthard Hoffmann; Achim Striebeck, both of Marl, Germany

[73] Assignee: Chemische Werke Huls Aktiengesellschaft, Marl, Germany

[22] Filed: July 29, 1974

[21] Appl. No.: 492,672

[30] Foreign Application Priority Data
Aug. 8, 1974 Germany............................ 2340047

[52] U.S. Cl. ........................ 260/346.4; 23/288 B; 55/96; 252/410; 252/411 R; 423/659
[51] Int. Cl.² ....................................... C07D 307/89
[58] Field of Search .............. 260/346.4; 252/411 R, 252/410; 55/96; 23/288 B; 423/659 H

[56] References Cited
UNITED STATES PATENTS
1,936,154  11/1933  Carter............................ 252/411 R
3,410,055  11/1968  Zenz......................................... 55/96

FOREIGN PATENTS OR APPLICATIONS
1,296,825  5/1962  France............................. 252/411
487,785  6/1938  United Kingdom OTHER PUBLICATIONS
Sherwood, The Industrial Chemist, Oct. 1959, p. 492–495.

Primary Examiner—Henry R. Jibes
Assistant Examiner—Bernard Dentz
Attorney, Agent, or Firm—Gilbert L. Wells

[57]  ABSTRACT

The method and apparatus for the oxidation of naphthalene to phthalic anhydride in multi-tube reactors having fixed bed catalysts therein are improved by removing deposits from the catalysts. These deposits are removed by impulsively decompressing the reactor in the direction of the inlet of the multi-tube reactor.

6 Claims, 2 Drawing Figures

REMOVAL OF DEACTIVATING DUST PARTICLES FROM FIXED BED CATALYSTS IN THE VAPOR PHASE OXIDATION OF NAPHTHALENE TO PHTHALIC ANHYDRIDE

CROSS REFERENCE TO A RELATED APPLICATION

Applicants claim priority under 35 U.S.C. 119 for Application Ser. No. P 23 40 047.7, filed Aug. 8, 1973 in the Patent Office of the Federal Republic of Germany.

BACKGROUND OF THE INVENTION

The field of the invention is polycarboxylic acid anhydrides prepared by oxidation of aromatic compounds.

The invention is particularly related to a method and apparatus for removing deposits from fixed-bed catalysts mounted in the tubes of multi-tube reactors (tube-nest or tube-cluster reactors). The removal of deposits restores the output to the levels prior to deposition.

The present invention is described in relation to the embodiment of the preparation of the anhydride of phthalic acid, however, the invention is effective wherever fixed-bed catalysts are mounted in multi-tube reactors and depositions occur in the course of the process.

Specifically the process for preparing the anhydride of phthalic acid is considered, wherein the crude naphthalene following tension evaporation in the presence of fixed-bed catalysts containing vanadium oxide is oxidized by means of gases containing oxygen, preferably air, to the anhydride of phthalic acid.

The state of the art of low-temperature fixed-bed air oxidation of naphthalene may be ascertained by reference to the Kirk-Othmer "Encyclopedia of Chemical Technology", Vol. 15 (1968), pages 448–457, and U.S. Pat. Nos. 1,285,117; 1,787,416; 1,787,417; 1,971,888; and 3,112,324, the disclosures of which are incorporated herein.

As pointed out by Kirk-Othmer, Vol. 15, at page 450, the low temperature fixed-bed air oxidation of naphthalene is carried out at 350° – 360°C with 4–5 second contact time. The catalyst is $V_2O_5$ on silica with 20–30 percent potassium sulfate.

When phthalic anhydride is manufactured on an industrial scale, crude naphthalene is used for economical considerations in lieu of pure naphthalene as the starting material, preferably being of the so-called hot-press material quality. The purity of this crude naphthalene is characterized by the freezing point, which fluctuates between 78° and 79°C and indicates a naphthalene content approximately between 95.5 and 97.5 percent. Coal tar derived crude naphthalene contains appreciable amounts of sulfur compounds, especially thionaphthene, as contaminations. It further contains phenolic substances and nitrogen compounds in varying amounts, also admixtures of slight amounts of inorganic compounds in the form of iron and alkali salts and residues of higher boiling points.

Because of these contaminants, crude naphthalene is generally tension vaporized in a partial stream of the reaction air, temperature being set between 130° and 160°C. During this tension vaporization, i.e., during a vaporization into the gas flowing over the crude naphthalene, not only does the concentration of the present impurities with higher boiling points increase in the vaporizer's sump, but also new amounts are formed by oxidation and resinification. These impurities may not be volatile at all, and furthermore, partly acid compounds may be formed as well. After a few weeks, the concentration of these substances in the sump of the tension vaporizer will rise to 50 percent and beyond before these residues are sluiced out together with the naphthalene still present.

Increasing tendency to foaming is observed as the naphthalene content drops in the vaporizer sumps, the air-stirred foam filling the empty space and the vaporizer components above the liquid level.

Gases containing oxygen, and in practice air alone, are used for the gaseous oxidation of naphthalene to the anhydride of phthalic acid, these gases streaming through the reactor from top to bottom while being laden with naphthalene. As a rule, supported catalysts are used, which will mainly support vanadium pentoxide as the effective substance. As regards the supports, one must distinguish between those substances which are inert in the sense of the reaction, for instance silicon carbide, porcelain or corundum, and those supports which control the catalytic activity of vanadium pentoxide, for instance silica gel or titanium dioxide in modifying anatase. Conventional activating additives are used in this respect too, for instance potassium pyrosulfate, by means of which the temperatures required for oxidation are lowered by approximately 80°–100°C. It is especially the last-named catalysts, the so-called "german-type contacts," which possess very long life besides high selectivity.

Despite this long catalyst life and even in the absence of selectivity degradation, the prior art catalysts have to be exchanged every few years because the flow resistance in the reactor pipes is so increased that the flow rate possible by means of the reaction air blowers falls below the economical values. There is even danger in the absence of catalyst exchange that the naphthalene transmission drops to such an extent that the heat of reaction no longer covers the radiative emission from the furnace and that therefore oxidation is no longer feasible.

Such a change of catalyst, which in this instance is required because of a decrease in activity, means not only interrupting manufacture for several weeks, but it also is very costly. Because of the great care required in filling thousands of tubes and in setting these to the same pressure gradient, catalyst change demands a great deal of labor.

On the basis of prior experience with other catalytic methods, expert opinion to date has always assumed that the cause of the increase in resistance of the reactor tubes filled with catalysts was due to the formation of catalyst dust or to the baking of the catalyst grains by means of deposited and incrusted reaction products.

SUMMARY OF THE INVENTION

Based upon comprehensive observations and tests, it has been found however that the resistance in multi-tube reactors increases because a constantly increasing layer of very fine dust is deposited on the catalyst in each tube, this dust essentially being inorganic in nature and consisting of iron oxide (ferric) and slight amounts of alkali salts. It is possible to determine the origin of this dust and it is the combustion residue of minute droplets of naphthalene enriched with naphthalene residue, this combustion residue being carried by the operational air out of the foaming naphthalene tension vaporizer. Under the reaction conditions, i.e., in general at a temperature between 360° and 400°C, in the presence of high oxygen excess and of a catalyst, the droplets' organic phase immediately burns, and the inorganic residue remains in the form of fine dust on the catalyst.

Having in mind this concept, it is an object of the present invention to remove this loose dust from the tubes of a reactor within the interval which is available before the temperature of the reactor, following oxidation termination, falls below that temperature value for which the reaction upon new addition of naphthalene and air can resume. This so-called resumption temperature depends upon the kind and age of the catalyst and lies between approximately 335° and 360°C. The time during which the reactor cools from the operational temperature of about 360° – 400°C to the resumption temperature generally does not exceed 12 – 15 hours.

Any foreseeable operation is hampered by the large number of reaction tubes operated in parallel. The number may be 3,000 – 5,000 for each reactor in the older models, but as many as 2,000 – 15,000 in the newer ones. Operation is further hampered by the high temperature of the upper tube bottom and by the requirement of relieving as evenly as possible all the pipes or tubes from the increased resistance.

This condition must be met on safety grounds. When a multiplicity of parallel operated reaction tubes is used, the distribution of the naphthalene-carrying reaction air takes place solely on the basis of the resistance present in each particular tube. Therefore, should the resistance of a given tube drop appreciably more when the dust resting upon the catalyst fill is removed than would be the case for the adjacent tubes, then the former one will be loaded appreciably more when operation resumes. The size of the heat exchange surfaces being the same for all reaction tubes, there is therefore a danger that the heat of reaction from the overloaded tube no longer can be transmitted sufficiently rapidly to the surrounding salt bath acting as a heat dissipator. The ensuing temperature rise therefore changes the selectivity of the catalyst and in the final state causes the burning of the naphthalene to carbon dioxide and water. The additional heat released thereby might even cause burning through the wall of a tube, so that the melt of saltpeter acting as heat dissipator could penetrate the reactor.

A method has been found according to the present invention for removing deposits from fixed-bed catalysts mounted in multiple tube reactors, which is characterized by excess pressure of a gas inert with respect to the catalysts and applied inside and to the rear of the multiple tube reactor which is impulsively decompressed in the direction of the inlet of the reactor.

A gas or a mixture of gases is suitably used for generating the excess pressure in the equipment, which is of such nature as not to damage the catalyst and is inert with respect to it. Inert gases such as nitrogen are generally applicable. In the case of the system for manufacturing phthalic anhydride, air is appropriate for generating the excess pressure.

The pressure to be built up inside and to the rear of the multiple tube reactors ranges from about 1 to 10, preferably from about 1.2 to 6 atmospheres absolute. The upper limit is set on one hand by the pressure tolerance of the equipment and on the other by the requirement to avoid expelling catalyst grains from the tubes during the implosion or impulsive decompression. The lower limit is set by the requirement of blowing the deposits off the catalyst grains. Therefore a minimum flow rate and a minimum time and a minimum amount of inert gases are required. If this minimum amount is not achieved by building up a sufficient pressure in the equipment, one may appropriately increase the amount by installing or connecting with a gas buffer chamber to the rear of the multiple tube reactor.

Decompression takes place in the direction opposite the flow of the reaction gases and during the catalytic reaction, appropriately against the external pressure. However, one may also use a system so that decomposition takes place against a pressure less than 1 atmosphere absolute. However, an additional expenditure in equipment is then required.

The multiple tube reactor remains at the operational temperature during the build-up of pressure and the subsequent impulsive decompression. Appropriately only the supply of the initial substances to be converted in the multiple tube reactor need be interrupted. This provides the advantage that upon removing the deposits in the multiple tube reactor, the chemical reaction immediately resumes.

It is of decisive significance for the achievement of the impulsive decompression as a step of the present invention that the relaxation of the built-up pressure take place through a sufficiently large cross section. Reference is made in this respect to one of many publications, namely, "Dimensioning pressure relief apertures for protection against chemical industry facilities in jeopardy of explosions", by Dr. H. J. Heinrich in Chemie-Ingenieur-Technik, 1966, pp 1125-33, and especially to page 1132, Table 4. Furthermore, this cross section is released impulsively, i.e., in as short a time as possible. In principle, any valve is applicable, wherein an aperture of large rated size is opened in the shortest time by spring action, pneumatic or electrical actuation.

Because of simplicity or reliability, it is advantageous to make use of a safety disk of large nominal size, which is mounted at the reactor inlet, for carrying out the decompression. In order to avoid having to raise the built-up pressure excess to the response pressure of this safety disk, the latter should be mechanically destroyed when the desired lower test pressure is reached, or else the operationally used safety disk should be previously replaced by another with a given lower response pressure. Employing decompression with the safety disk that is present offers the special advantage that the full cross section of the relief aperture is opened instantaneously. Again reference is made in this instance to loc cit, page 1125, right column, for the statement that the optimum decompression for purposes of and when using the safety disk present in the equipment is used, identical in this instance with the so-called bursting membrane, decompression occurs practically without delay. It is therefore especially appropriate for the implementation of the procedure of the invention to use the existing safety disk or a replacement therefore. A similarly rapid and effective aperture of a pipe connector of large size may be achieved by means of sliders or flaps, even when actuated elastically, pneumatically or electrically, but at much greater cost.

In order to determine the most favorable operation for the individual multiple tube reactor, removal of the deposits appropriately starts for the built-up pressure in the lower range set by the above limits. The multiple tube reactor thereupon is put into operation again and is tested for satisfactory performance. If required, pressure build-up and decompression in impulsive manner is then repeated at higher values, if appropriate by hooking up a gas buffer chamber to the rear of the multiple tube reactor. This is feasible because both pressure build-up and impulsive decompression require only a very minor expenditure.

BRIEF DESCRIPTION OF THE DRAWINGS

The figures of the drawings appended herewith illustrate in non-limiting manner the method and apparatus of the present invention and represent one embodiment thereof.

DESCRIPTION OF THE PREFERRED EMBODIMENTS

Figure 1:
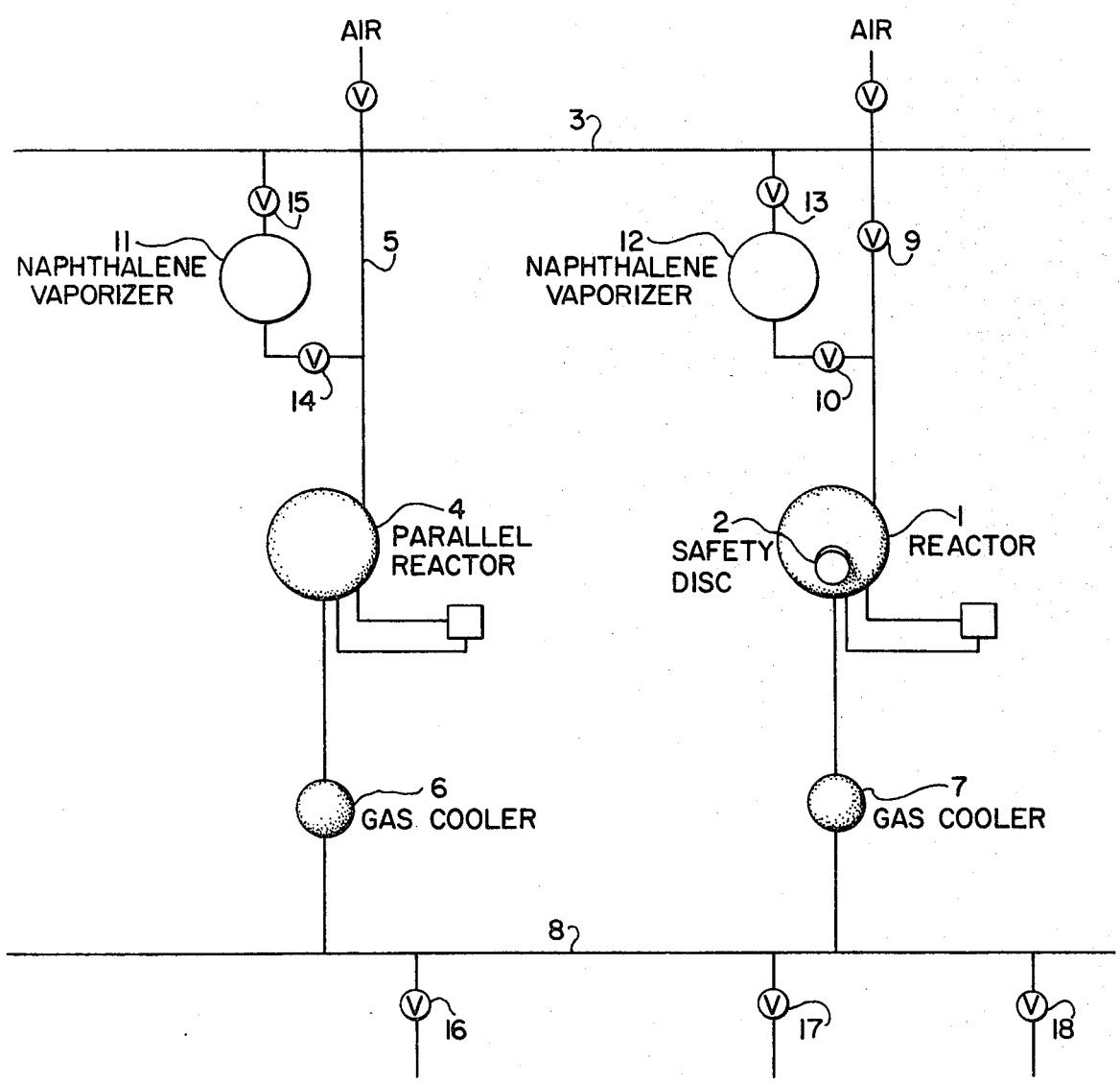
FIG. 1 is a schematic topview of the apparatus of the present invention for carrying out the oxidation of naphthalene to phthalic anhydride having two paths.
Figure 2:
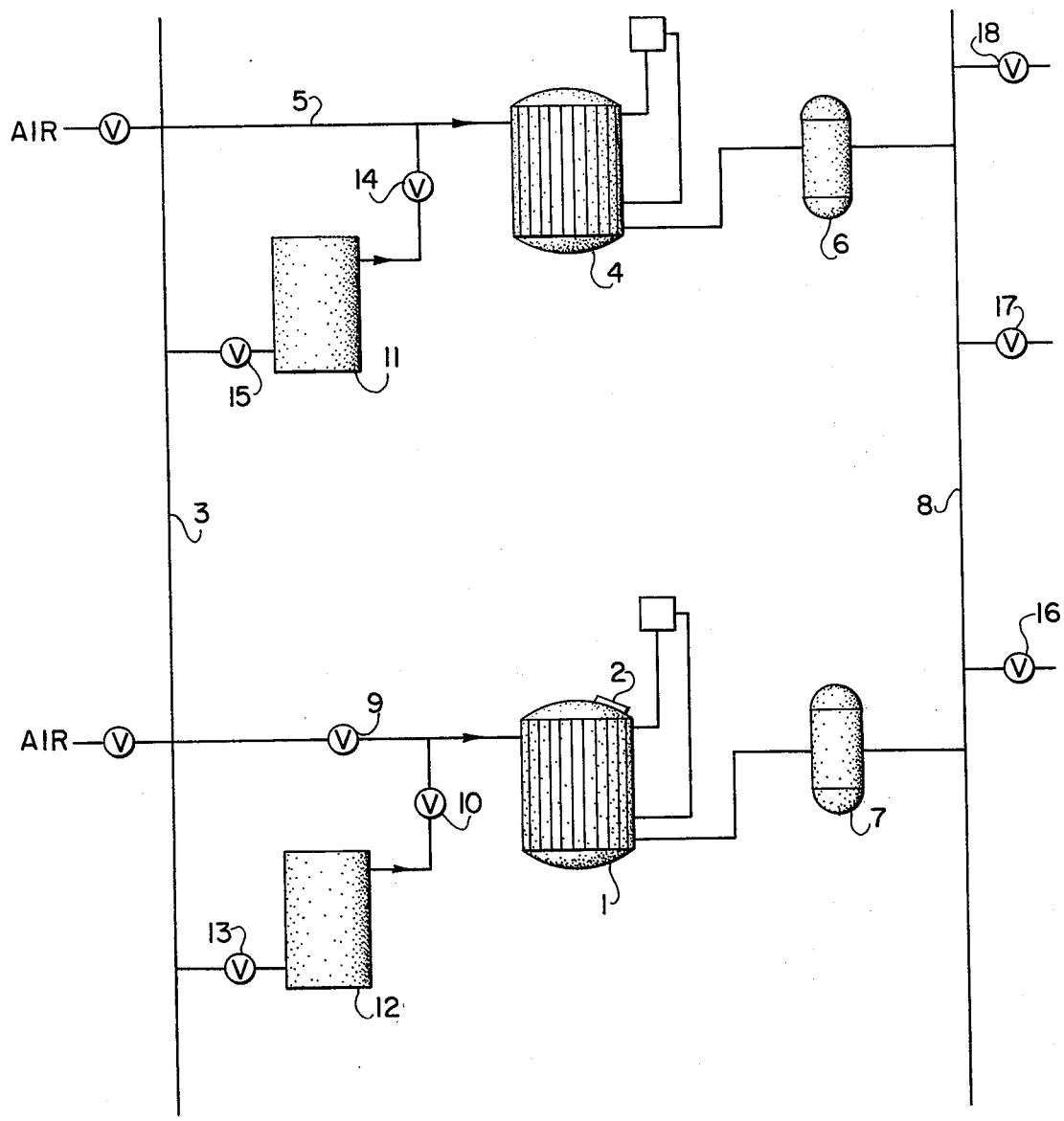
FIG. 2 is a schematic sideview of the apparatus of FIG. 1.

The invention is best described by reference to a specific example of carrying out the process in the embodiment of the apparatus shown in the drawings, wherein:

A reactor for manufacturing phthalic anhydride and comprising 4,450 tubes 3,000 mm long and of nominal width of 25 mm, being filled with the usual solid bed catalyst containing vanadium oxide for the purpose of naphthalene oxidation, was operated under a load of 1.66 cubic meters air at standard temperature and pressure per hour and per tube for a salt bath temperature of 396°–368°C. Tension vaporized crude naphthalene was admixed to the reaction air at a rate of 42 grams per cubic meter at standard temperature and pressure. Under these conditions of reaction, a total pressure indicated by a 4,800 mm column of water, i.e., about 0.48 atmosphere gauge, was measured shortly upon start of the operation, that is, after filling the tubes with a new catalyst.

In the course of 96 months of operation, the system resistance gradually increased, while yield and quality of the reaction product remained unchanged. For the same blower supply pressure indicated by a 7,200 mm column of water and the same naphthalene loading of 42 grams per cubic meter at standard temperature and pressure, only a load of 1.12 cubic meters at standard temperature and pressure of reaction air per hour and per tube could be maintained. Despite the transmission being reduced to 67.5 percent, the pressure at the reactor had increased to a pressure indicated by a 6,950 mm water column. At this time, restoration of the initial production capacity, i.e., of reactor performance, was carried out in accordance with the method of the present invention without changing the catalyst.

The facility being shut off, first the inlet safety disk 2 of rated width of 500 mm of reactor 1 and designed for a bursting pressure indicated by a 8,000 mm water column, was exchanged for a disk with a design pressure indicated by a 4,500 mm water column. Then pressure was applied from the blower main 3 at a controlled pressure indicated by a 7,200 mm water column via line 5 leading to the parallel operating reactor 4, which in this case sets as a gas reservoir, and via gas coolers 6 and 7 and the intervening crystal separator manifold 8, to reactor 1, said pressure being slowly applied up to the air shut-off valves 9 and 10.

As a safety measure, the naphthalene evaporators 11 and 12 were previously shut off by valves 10, 13, and 14, 15. The gas valves 16, 17 and 18 leading to the crystal separators also were shut.

For a pressure indicated by 4,000 – 4,200 mm water column at the inlet of reactor 1, the safety disk 2 was spontaneously expelled, a cloud of brown dust being noticeably blown out of the safety disk connecting pipe.

Upon resuming operation, it was found that the conditions relating to resistance in the tubes of the multi-tube reactor had been widely normalized. For a rate of 1.66 cubic meters at standard temperature and pressure of naphthalene-laden reaction air per tube and per hour, which did not involve an increase in blower pressure, the pressure measured at the reactor amounted only to 6,000 mm water column. Yield and qualtiy of the reaction with respect to the end product remained as good as before.

We claim:

1. In a method where vapors of naphthalene are partially oxidized in a multi-tube reactor having fixed-bed catalysts therein to produce gaseous reaction products containing phthalic anhydride and deactivating dust particles deposited on the surface of said fixed-bed catalysts, the improvement comprising building up excess pressure in and to the rear of said multi-tube reactor, said excess pressure inert with respect to said catalysts, and impulsively decompressing said reactor in the direction of the reactor inlet and removing said deactivating dust particles from the surface of said catalysts.

2. The method of claim 1, wherein said excess pressure built up in and to the rear of said reactor is from about 1 to 10 atmospheres absolute.

3. The method of claim 2, wherein said impulsive decompression is effected by applying said excess pressure to a safety disk in said reactor at a bursting pressure.

4. The method of claim 3, wherein said bursting pressure is about 1.2 – 6 atmospheres absolute.

5. The method of claim 1, wherein said built up pressure is accomplished by applying gas pressure.

6. The method of claim 5, wherein said gas pressure applied is air.

* * * * *